United States Patent [19]

Genshaw et al.

[11] Patent Number: 5,620,579

[45] Date of Patent: Apr. 15, 1997

[54] APPARATUS FOR REDUCTION OF BIAS IN AMPEROMETRIC SENSORS

[75] Inventors: Marvin A. Genshaw, Elkhart; Dijia Huang; Matthew K. Musho, both of Granger; Kin F. Yip, Elkhart, all of Ind.

[73] Assignee: Bayer Corporation, Elkhart, Ind.

[21] Appl. No.: 435,993

[22] Filed: May 5, 1995

[51] Int. Cl.$^6$ .................. G01N 27/26; G01N 27/327
[52] U.S. Cl. ............ 204/402; 204/403; 205/775; 205/777.5
[58] Field of Search .................. 204/402, 403, 204/406; 205/775, 777.5

[56] References Cited

U.S. PATENT DOCUMENTS

| | | | |
|---|---|---|---|
| 4,496,454 | 1/1985 | Berger | 204/402 |
| 4,746,607 | 5/1988 | Mura et al. | 435/25 |
| 4,853,091 | 8/1989 | Mund et al. | 204/403 |
| 4,929,545 | 5/1990 | Freitag | 435/11 |
| 5,112,455 | 5/1992 | Cozzette et al. | 204/402 |
| 5,288,387 | 2/1994 | Ito et al. | 204/403 |
| 5,288,636 | 2/1994 | Pollmann et al. | 435/288 |
| 5,456,811 | 10/1995 | Edwards et al. | 204/402 |

FOREIGN PATENT DOCUMENTS

| | | |
|---|---|---|
| 0330517 | 2/1989 | European Pat. Off. . |
| 0354441 | 8/1989 | European Pat. Off. . |

OTHER PUBLICATIONS

Analytica Chimica Acta. 140 (1982) month unavailable 1–18, Fultz et al. "Mediator Compounds for the Electrochemical Study of Biological Redox Systems: A Compilation".

Clinica Chimica Acta., 57 (1974) month unavailable 283–289, Schläpfer et al "Electrochemical Measurement of Glucose Using Various Electron Acceptors".

Primary Examiner—T. Tung
Attorney, Agent, or Firm—Jerome L. Jeffers

[57] ABSTRACT

Apparatus and method are provided for determining the concentration of an analyte in a fluid test sample by applying the fluid test sample to the surface of a working electrode which is electrochemically connected to a reference electrode which surface bears a composition comprising an enzyme specific for the analyte. A mediator is reduced in response to a reaction between the analyte and the enzyme. An oxidizing potential is applied between the electrodes to return at least a portion of the mediator back to its oxidized form before determining the concentration of the analyte to thereby increase the accuracy of the analyte determination. Following this initially applied potential, the circuit is switched to an open circuit or to a potential that substantially reduces the current to minimize the rate of electrochemical potential at the working electrode. A second potential is applied between the electrodes and the current generated in the fluid test sample is measured to determine analyte concentration. Optionally, the accuracy of the analyte determination is further enhanced algorithmically.

5 Claims, 3 Drawing Sheets

APPARATUS FOR REDUCTION OF BIAS IN AMPEROMETRIC SENSORS

FIELD OF THE INVENTION

The present invention generally relates to a biosensor, and, more particularly, to a new and improved method and apparatus for reducing bias in amperometric sensors.

BACKGROUND OF THE INVENTION

The quantitative determination of analytes in body fluids is of great importance in the diagnoses and maintenance of certain physiological abnormalities. For example lactate, cholesterol and bilirubin should be monitored in certain individuals. In particular, the determination of glucose in body fluids is of great importance to diabetic individuals who must frequently check the level of glucose in their body fluids as a means of regulating the glucose intake in their diets. While the remainder of the disclosure herein will be directed towards the determination of glucose, it is to be understood that the procedure and apparatus of this invention can be used for the determination of other analytes upon selection of the appropriate enzyme. The ideal diagnostic device for the detection of glucose in fluids must be simple, so as not to require a high degree of technical skill on the part of the technician administering the test. In many cases, these tests are administered by the patient which lends further emphasis to the need for a test which is easy to carry out. Additionally, such a device should be based upon elements which are sufficiently stable to meet situations of prolonged storage.

Methods for determining analyte concentration in fluids can be based on the electrochemical reaction between the analyte and an enzyme specific to the analyte and a mediator which maintains the enzyme in its initial oxidation state. Suitable redox enzymes include oxidases, dehydrogenases, catalase and peroxidase. For example, in the case where glucose is the analyte, the reaction with glucose oxidase and oxygen is represented by equation (A).

In a colorimetric assay, the released hydrogen peroxide, in the presence of a peroxidase, causes a color change in a redox indicator which color change is proportional to the level of glucose in the test fluid. While colorimetric tests can be made semi-quantitative by the use of color charts for comparison of the color change of the redox indicator with the color change obtained using test fluids of known glucose concentration, and can be rendered more highly quantitative by reading the result with a spectrophotometric instrument, the results are generally not as accurate nor are they obtained as quickly as those obtained using a biosensor. As used herein, the term biosensor is intended to refer to an analytical device that responds selectively to analytes in an appropriate sample and converts their concentration into an electrical signal via a combination of a biological recognition signal and a physico-chemical transducer. Aside from its greater accuracy, a biosensor is an instrument which generates an electrical signal directly thereby facilitating a simplified design. In principle, all the biosensor needs to do is measure the time and read the current. Furthermore, a biosensor offers the advantage of low material cost since a thin layer of chemicals is deposited on the electrodes and little material is wasted.

Referring to the above equation (A), a suitable electrode can measure the formation $H_2O_2$ due to its introduction of electrons into the test fluid according to equation B:

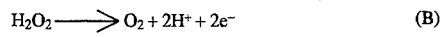

The electron flow is then converted to the electrical signal which directly correlates to the glucose concentration.

In the initial step of the reaction represented by equation (A), glucose present in the test sample converts the oxidized flavin adenine dinucleotide (FAD) center of the enzyme into its reduced form, (FADH$_2$). Because these redox centers are essentially electrically insulated within the enzyme molecule, direct electron transfer to the surface of a conventional electrode does not occur to any measurable degree in the absence of an unacceptably high cell voltage. An improvement to this system involves the use of a nonphysiological redox coupling between the electrode and the enzyme to shuttle electrons between the (FADH$_2$) and the electrode. This is represented by the following scheme in which the redox coupler, typically referred to as a mediator, is represented by M:

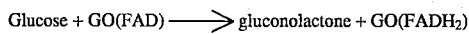

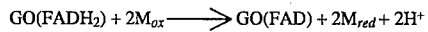

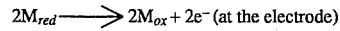

In the scheme, GO(FAD) represents the oxidized form of glucose oxidase and GO(FADH$_2$) indicates its reduced form. The mediating species $M_{ox}/M_{red}$ shuttles electrons from the reduced enzyme to the electrode thereby oxidizing the enzyme causing its regeneration in situ which, of course, is desirable for reasons of economy. The main purpose for using a mediator is to reduce the working potential of the sensor. An ideal mediator would be reoxidized at the electrode at a low potential under which impurity in the chemical layer and interfering substances in the sample would not be oxidized thereby minimizing interference.

Many compounds are useful as mediators due to their ability to accept electrons from the reduced enzyme and transfer them to the electrode. Among the mediators known to be useful as electron transfer agents in analytical determinations are the substituted benzo- and naphthoquinones disclosed in U.S. Pat. No. 4,746,607; the N-oxides, nitroso compounds, hydroxylamines and oxines specifically disclosed in EP 0 354 441; the flavins, phenazines, phenothiazines, indophenols, substituted 1,4-benzoquinones and indamins disclosed in EP 0 330 517 and the phenazinium/ phenoxazinium salts described in U.S. Pat. No. 3,791,988. A comprehensive review of electrochemical mediators of biological redox systems can be found in *Analytica Clinica Acta.* 140 (1982), Pp 1–18.

Among the more venerable mediators is hexacyanoferrate, also known as ferricyanide, which is discussed by Schläpfer et al in *Clinica Chimica Acta.,* 57 (1974), Pp. 283–289. In U.S. Pat. No. 4,929,545 there is disclosed the use of a soluble ferricyanide compound in combination with a soluble ferric compound in a composition for enzymatically determining an analyte in a sample. Substituting the iron salt of ferricyanide for oxygen in equation (A) provides:

Glucose + 2 Fe$^{+++}$(CN)$_6$$^{3-}$ $\xrightarrow{GO}$ gluconolactone + 2 Fe$^{++}$(CN)$_6$$^{4-}$ since the ferricyanide is reduced to ferrocyanide by its acceptance of electrons from the glucose oxidase enzyme.

Another way of expressing this reaction is by use of the following equation (C):

Glucose + GO(FAD) $\longrightarrow$ gluconolactone + GO(FADH$_2$)  (C)

GO(FADH$_2$) + 2 Fe(CN$_3$)$_6$$^{3-}$ $\longrightarrow$

GO(FAD) + 2 Fe(CN)$_6$$^{4-}$ + 2H$^+$

2 Fe(CN)$_6$$^{4-}$ $\longrightarrow$ 2 Fe(CN)$_6$$^{3-}$ + 2e$^-$ (at the electrode)

The electrons released are directly equivalent to the amount of glucose in the test fluid and can be related thereto by measurement of the current which is produced through the fluid upon the application of a potential thereto. Oxidation of the ferrocyanide at the anode renews the cycle.

As is apparent from the above description, a necessary attribute of a mediator is the ability to remain in the oxidized state under the conditions present on the electrode surface prior to the use of the sensor. Any reduction of the mediator will increase the background current resulting in the biosensor reading being biased. It has been discovered that these mediators do tend to be reduced over time, especially under conditions of stress, thereby diminishing the usefulness of the sensors to which they are applied.

In published international patent application PCT/US92/01659 there is disclosed the use of potassium dichromate as an oxidizing agent in a colorimetric reagent strip. The purpose of the oxidizing agent is to oxidize impurities in other reagent components to improve the colorimetric sensor's stability. This publication mentions U.S. Ser. No. 07/451,671 (now U.S. Pat. No. 5,288,636) and characterizes it as describing a system in which a reduced mediator is re-oxidized by the application of a potential and measuring the current after a specific time to determine the concentration of the analyte. More specifically, the '636 patent requires the complete oxidation of the glucose by glucose oxidase. As the enzyme is reduced by the glucose, the ferricyanide reacts with enzyme to produce ferrocyanide. The ferrocyanide produced by this enzymatic reaction is combined with ferrocyanide produced during storage. This latter ferrocyanide is the result of a reaction between ferricyanide and impurities found in materials deposited with the glucose oxidase and ferricyanide. The '636 patent makes no distinction between ferrocyanide produced between these two sources.

It would be desirable, and it is an object of the present invention to provide a method whereby the undesired reduction of mediator compounds stored on an electrodes surface can be reversed to minimize its effect on estimating the analyte values in fluid test samples with very low analyte concentrations.

It is a further object to provide such a method in which the accuracy of the analyte determination is enhanced.

It is a further object to provide such a method wherein the analyte is glucose.

An additional object is to provide a mathematical means for further enhancement of the accuracy of the analyte determination.

It is a further object to provide apparatus for accurately determining analyte values.

It is a further object to provide such apparatus that is simple and economical to manufacture.

SUMMARY OF THE INVENTION

The present invention involves a method for determining the concentration of an analyte in a fluid test sample by applying the test sample to the surface of a working electrode. The electrode has on its surface a composition comprising an enzyme specific for the analyte, a mediator which is reduced as a result of a reaction between the analyte and the enzyme, which mediator has undergone partial reduction to its reduced state as a result of having been exposed to ambient conditions. There is disclosed herein an improvement to the method which involves the steps of:

a) applying a positive potential pulse to the electrode to oxidize at least a portion of the mediator to its oxidized form. This step reduces background bias in the electrode. The background bias can be further reduced by:

a) determining the current ($i_1$) during the application of the positive pulse and the current ($i_2$) at the end of the read time, and b) calculating the corrected analyte level G by solving equation (1):

$$G = \frac{i_2 - Int}{slope} - k \cdot \Delta(i_1, i_2) \qquad (1)$$

where Int and slope are the intercept and slope of $i_2$ and $\Delta(i_1, i_2)$ is an error correction term proportional to the background bias calculated as:

$$\Delta(i_1, i_2) = \frac{Int}{slope} \cdot \left( \frac{slope \cdot i_1 - s_1 \cdot i_2}{slope \cdot i_{1\_lo} - s_1 \cdot i_{2\_1l}} - 1 \right) \qquad (2)$$

where $s_1$ = slope of $i_1$
$i_{1-lo} = i_1$ at a low analyte level,
$i_{2-lo} = i_2$ at a low analyte level, and
k = a selected scaling factor.

BRIEF DESCRIPTION OF THE DRAWINGS

The present invention together with the above and other objects and advantages may best be understood from the following detailed description of the preferred embodiments of the invention illustrated in the drawings, wherein.

DESCRIPTION OF THE INVENTION

The present invention is a method that reduces the background bias due to oxidizable impurities in an amperometric sensor used for measuring a specific analyte, such as glucose, in blood. The background current of such a sensor will increase if it is stored over a long period of time or under stress (heat, moisture, etc.) due to the increased presence of reduced mediator or other reduced impurity present in the sensor such as enzyme stabilizers, e.g. glutamate, and surfactants having reducing equivalents. For example, in a ferricyanide based amperometric sensor, the background bias is related to the presence of ferrocyanide (from the reduction of ferricyanide) near the electrode surface. This accumulated ferrocyanide, as opposed to the ferrocyanide produced during use of the sensor (fresh ferrocyanide), is oxidized back to ferricyanide to reduce the background bias it causes and thereby extend the sensor shelf life. To achieve this objective, the method uses an electrochemical approach. The background bias is further reduced when the electrochemical approach is augmented with an algorithmic correction.

Figure 1A:
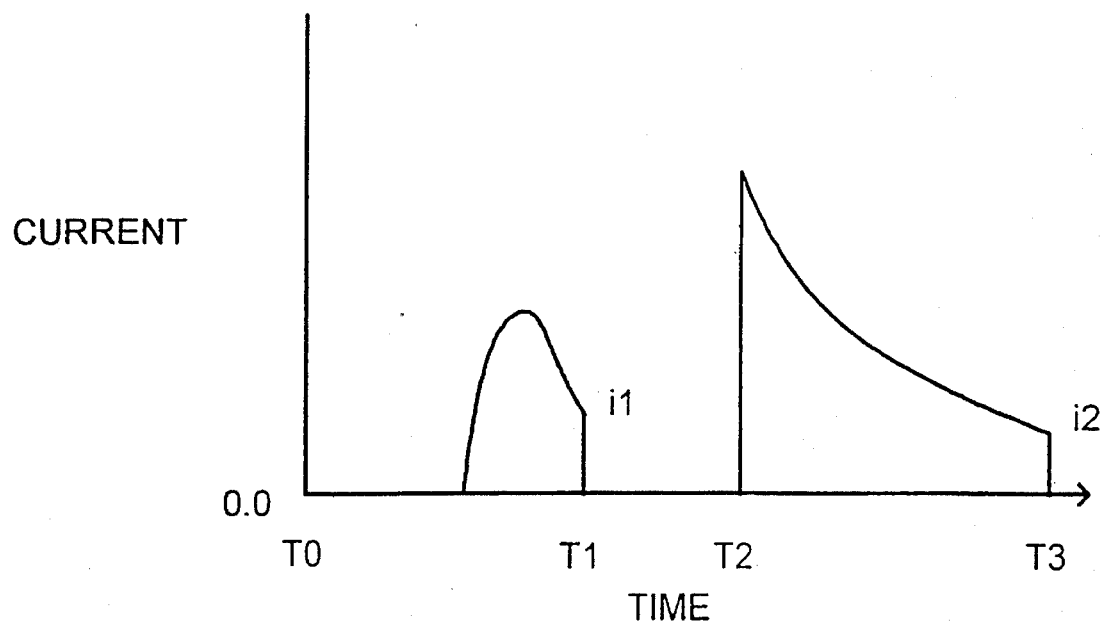
FIGS. 1A and 1B are charts illustrating potential and current relative to time respectively in accordance with the method of the invention.
Figure 1B:
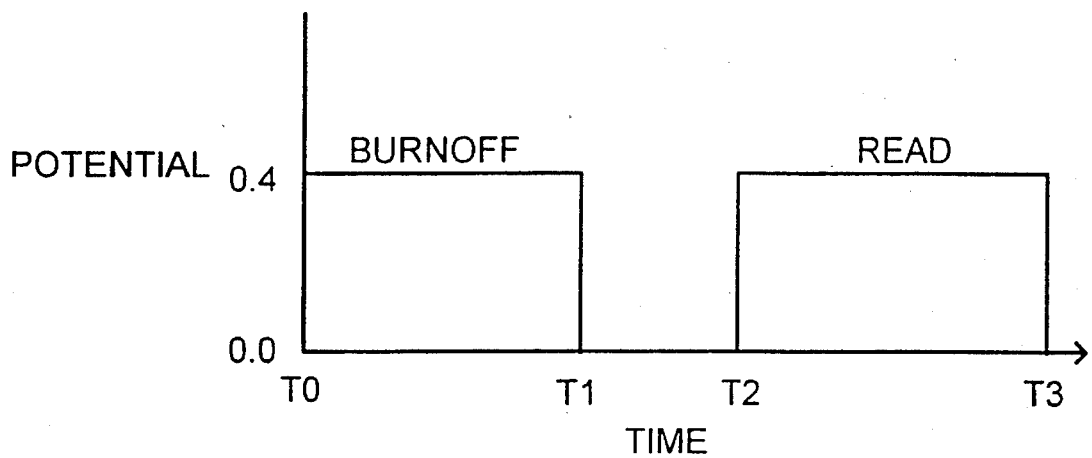

Referring to FIGS. 1A and 1B, the method of our invention involves first applying a positive potential pulse (called the "burn-off" pulse) which precedes the normal potential profile during use of the sensor. This is typically accomplished by applying a positive potential of from 0.1 to 0.9 volt (preferably 0.3 to 0.7 volt) between the working and reference electrodes of the sensor for a period of from 1 to 15 seconds (preferably 5 to 10 seconds). The burn-off pulse oxidizes the initial ferrocyanide (or other oxidizable impurity), so that the sensor can begin the assay with a clean background. Typically, the background is not perfectly clean since only a portion of the oxidizable impurity is oxidized by the burn-off pulse. This is the case because the chemical layer covers both the working and the reference electrodes. The initial ferrocyanide exists in the chemical layer since it comes from ferricyanide. When sample fluid is applied and the chemical layer re-hydrates, the ferrocyanide near the working electrode is re-oxidized. The rest of the ferrocyanide diffuses into the sample fluid and is mixed with the glucose. That portion of the initial ferrocyanide cannot be re-oxidized without affecting the glucose. The initial ferrocyanide is near the electrode for a very short time (a few seconds) after the fluid test sample is applied. The reason for this is that the chemicals (enzyme and ferricyanide, etc.) are deposited as a thin layer on the working and reference electrodes. The burn-off technique takes advantage of this since a significant amount of the initial ferrocyanide can be burned off without noticeable reduction of the analyte concentration in the fluid test sample most of which does not come into direct contact with the electrode. Experiments have demonstrated that the background bias of a stressed sensor can be reduced by 40% with proper application of the burn-off pulse.

The background bias can be further reduced by the use of a background correction algorithm which works in conjunction with the burn-off pulse. The algorithm is based on the taking of two current readings. The first reading ($i_1$) is taken during the burn-off pulse and the second ($i_2$) at the end of the read time, i.e. the time elapsed from the moment when the second potential pulse is applied to the moment when the current $i_2$ is measured. The length of the read time is $t_3-t_2$, as shown in FIG. 1. The analyte concentration is then calculated from the two current readings, $i_1$ and $i_2$. Tests on sensors have shown that the background correction algorithm is able to remove at least 80% of the remaining background bias, and, as a result, the sensor stability can be improved to provide a significant extension in shelf life.

An amperometric glucose sensor of the type useful in the practice of the present invention is constructed as follows: Two carbon electrodes are printed on a polymer substrate. Next a layer of chemical components is deposited on the electrodes and dried. A preferred chemical composition is 5 μL of a medium containing 55 mM ferricyanide (potassium salt), 8.5 units of glucose oxidase, 0.53% of poly(ethylene oxide), 0.40% of cremophor as surfactant and 83 mM phosphate buffer at pH 7.2. During the glucose assay, a potential profile consisting of three consecutive time periods is applied to the sensor. These time periods are, in sequence, the burn-off time (typically 0.4 volt for 10 seconds); delay period (open circuitry for 15 seconds) and read time (0.4 volts, 5 seconds). The exact time of the delay period is not critical but is normally in the range of 10 to 40 seconds. This delay period allows sufficient time for the reaction to build up sufficient ferrocyanide to allow the current resulting from the reoxidation of the ferrocyanide to be measured without difficulty. These time periods are illustrated in FIGS. 1A and 1B which plots potential and current against time. Current measurements are taken at the end of the burn-off period ($i_1$) and read time ($i_2$) whereupon the corresponding glucose concentration is calculated using equation 1. The constants in the equation, e.g. slopes and intercepts are predetermined values.

The following discussion relates to a fluid test sample in which glucose is the analyte to be detected and involves a sensor in which ferricyanide is the mediator. However, the discussion is equally applicable to systems for the determination of other analytes and in which the oxidizable species is something other than ferrocyanide.

The burn-off technique, i.e. application of a positive potential pulse to the electrode to oxidize at least a portion of the mediator back to its oxidized form, is illustrated by FIGS. 1A and 1B. In FIGS. 1A and 1B, in which the potential and current profiles are plotted, the timing is as follows:

$t_0$—sample is detected, burnoff period begins. Sample is detected by inserting the sensor into the instrument which causes the immediate application of a 0.4 volt potential. The current is continuously checked to see if a larger than predetermined. threshold (e.g. 250 nA) is measured. When a larger current than the threshold value is detected, a sample has been detected to begin the burnoff time period.

$t_1$—end of burn-off period and current $i_1$ is measured. The length of the burnoff period, $t_1-t_0$, is usually 5 to 10 seconds. The potential is 0.4 volt at $t_1$ but switches to an open circuit or to a potential that substantially reduces the current to minimize the rate of electrochemical reaction at the working electrode for a set delay period after the burnoff period.

$t_2$—end of set delay period. The length of the wait period, $t_2-t_1$, is normally 10 to 40 seconds. A read potential of 0.4 volt is applied at $t_2$.

$t_3$—end of read time when current $i_2$ is measured. The length of the read time, $t_3-t_2$, is 5 to 10 seconds.

The burn-off pulse, i.e. application of the 0.4 volt potential from $t_0$ to $t_1$, is designed to eliminate part of initial ferrocyanide (accumulated ferro) or other oxidizable interferents in the enzyme layer.

The burn-off algorithm calculates glucose concentration from two current measurements $i_1$ and $i_2$ using equation 1:

$$G = \frac{i_2 - Int}{slope} - k \cdot \Delta(i_1, i_2) \quad (1)$$

where $$\Delta(i_1, i_2) = \frac{Int}{slope} \cdot \left( \frac{slope \cdot i_1 - s_1 \cdot i_2}{slope \cdot i_{1\_lo} - s_1 \cdot i_{2\_1l}} - 1 \right) \quad (2)$$

Equation 1 is a partial correction algorithm which is intended to achieve a compromise between reducing stress-related background bias and preserving system precision. The basic scheme is to use $i_2$ as a glucose reading $$G = \frac{I_2 - \text{int}}{\text{slope}}$$

where int and slope are the intercept and slope of $i_2$ respectively. The term $\Delta(i_1,i_2)$ is the estimated background increase, due to stress or other causes, derived from the current $i_1$ and $i_2$. For fresh sensors, this term is close to zero. The parameter k is selectively provided or set to a value from 0 to 1. There will be no background correction if k is set at zero. On the other hand a full correction can be achieved if k is 1. In the following examples k is set at 0.8 for partial correction because it has been found that the variation of $i_1$ is larger than that of $i_2$ when multiple sensors are tested under the same glucose concentration. Compared with the glucose value calculated from $i_2$ alone, k=0 in equation (1), the glucose value calculated from $i_1$ and $i_2$ jointly will be slightly lower in precision (a larger standard deviation) and, of course, a much smaller background bias. The tradeoff between the precision and bias can be achieved by choosing the proper k value. If k=0, there is no background correction and $i_1$ is not used. In this case, the highest precision can be obtained, but it is accompanied by a high background bias. If k=1, the full background correction is applied whereupon the lowest bias can be achieved but at the cost of precision. The k value is set at 0.8 in the example to achieve a compromise between precision and bias.

The parameters in these equations are:

Int—intercept of read current $i_2$, nA.
slope—slope of read current $i_2$, nA·dL/mg.
$i_{1\_lo}$—average burn-off current $i_1$, nA, at the low glucose calibration level, i.e. 50 mg/dL.
$i_{2\_lo}$—average read time current $i_2$, nA, at the low glucose calibration level. Actually, $i_{2\_lo}$ is not an independent parameter. It can be calculated from Int and slope:

$$i_{2\_lo} = \text{Int} + \text{slope} \cdot 50.$$

$s_1$—slope of burn-off currently, nA·dL/mg.
k—set to 0.8 for partial correction.
Int, slope, $i_{1\_lo}$, and $s_1$ are local parameters; each sensor lot has its own parameter values which values are determined experimentally. The algorithm needs two known current values, one for $i_1$ and one for $i_2$ for normal (unstressed) sensors. The $i_{1\_lo}$ and $i_{2\_lo}$ are available since they are used in determining the intercept (Int) and slopes ($s_1$ and slope). Of course, current at other glucose levels can be used in the algorithm. This would however introduce the extra step of adding two additional independent parameters. The procedure of the present invention is demonstrated in the following examples:

EXAMPLE I

The following steps are taken to determine the lot parameter values necessary in the algorithm:

A. Test 16 sensors from the lot at the low calibration level, 50 mg/dL, and obtain the average currents $i_{1\_lo}$ and $i_{2\_lo}$ of the burn-off current and read time current, respectively. It is found that $i_{1\_lo}$=1951.2 nA and $i_{2\_lo}$=1952.3 nA.

B. Test 16 sensors at the high calibration level, 400 mg/dL, and obtain the average current $i_{1\_hi}$ and $i_{2\_hi}$. It is found that $i_{1\_hi}$=6003.3 nA and $i_{2\_hi}$=8831.7 nA.

C. Calculate the parameter values:

$$\text{Int} = i_{2\_lo} - \frac{50 \cdot (i_{2\_hi} - i_{2\_lo})}{350} =$$

$$1952.3 - \frac{50 \cdot (8831.7 - 1952.3)}{350} = 969.5 \text{ nA}$$

$$\text{slope} = \frac{i_{2\_hi} - i_{2\_lo}}{350} = \frac{8831.7 - 1952.3}{350} = 19.65 \text{ nA} \cdot \text{dL/mg}$$

$$s_1 = \frac{i_{1\_hi} - i_{1\_lo}}{350} = \frac{6003.3 - 1951.2}{350} = 11.58 \text{ nA} \cdot \text{dL/mg}$$

Therefore, equation (1) becomes:

$$G = \frac{i_2 - 969.5}{19.65} - 0.8 \cdot \Delta(i_1, i_2)$$

$$\Delta(i_1, i_2) = \frac{969.5}{19.65} \cdot \left( \frac{19.65 \cdot i_1 - 11.58 \cdot i_2}{19.65 \cdot 1951.2 - 11.58 \cdot 1952.3} - 1 \right)$$

$$= 0.06162 \cdot i_1 - 0.03631 \cdot i_2 - 49.34$$

EXAMPLE II

It has been discovered that the burn-off pulse alone will significantly reduce the background bias even without the use of the background correction algorithm.

In this experiment, ten sensors were stressed under 30° C. and 91% humidity for 3 hours. Aqueous glucose at 50 mg/dL was used as sample. Five stressed sensors were tested with a 10 second burn-off pulse and five without the pulse. In addition, ten unstressed sensors were tested as control (five with the 10 second burn-off and five without) and the bias calculated using the following equation (3):

$$\text{bias} = \frac{i_{stressed} - i_{unstressed}}{i_{unstressed}} \times 100\% \quad (3)$$

It was found that the bias was 30.6% without the burn-off pulse and 18.0% with it which data demonstrate that the burn-off pulse alone reduces the background bias by about 40%.

EXAMPLE III

This example explains how the algorithm corrects for background bias:

Eight sensors were stored at below −20° C. for two weeks and another eight sensors were stressed at 50° C. for four weeks. All sixteen sensors were tested using whole blood having a 100 mg/dL glucose concentration. The parameter values were determined from fresh sensors. The glucose readings, G, were calculated as follows:

A. No background bias correction algorithm: Equation 1 with k=0.

B. Partial correction: Equation 1 with k=0.8.

The bias in percent is calculated using Equation 4 with the results being listed in Table 1.

TABLE 1

$$\text{bias} = \frac{G - 100}{100} \times 100\% \quad (4)$$

Bias at 100 mg/dL

| | no burn-off algorithm | Partial correction (k = 0.8) |
|---|---|---|
| −20° C., 2 weeks | 3.8% | 5.3% |
| 50° C., 4 weeks | 64.7% | 15.0% |

Figure 2:
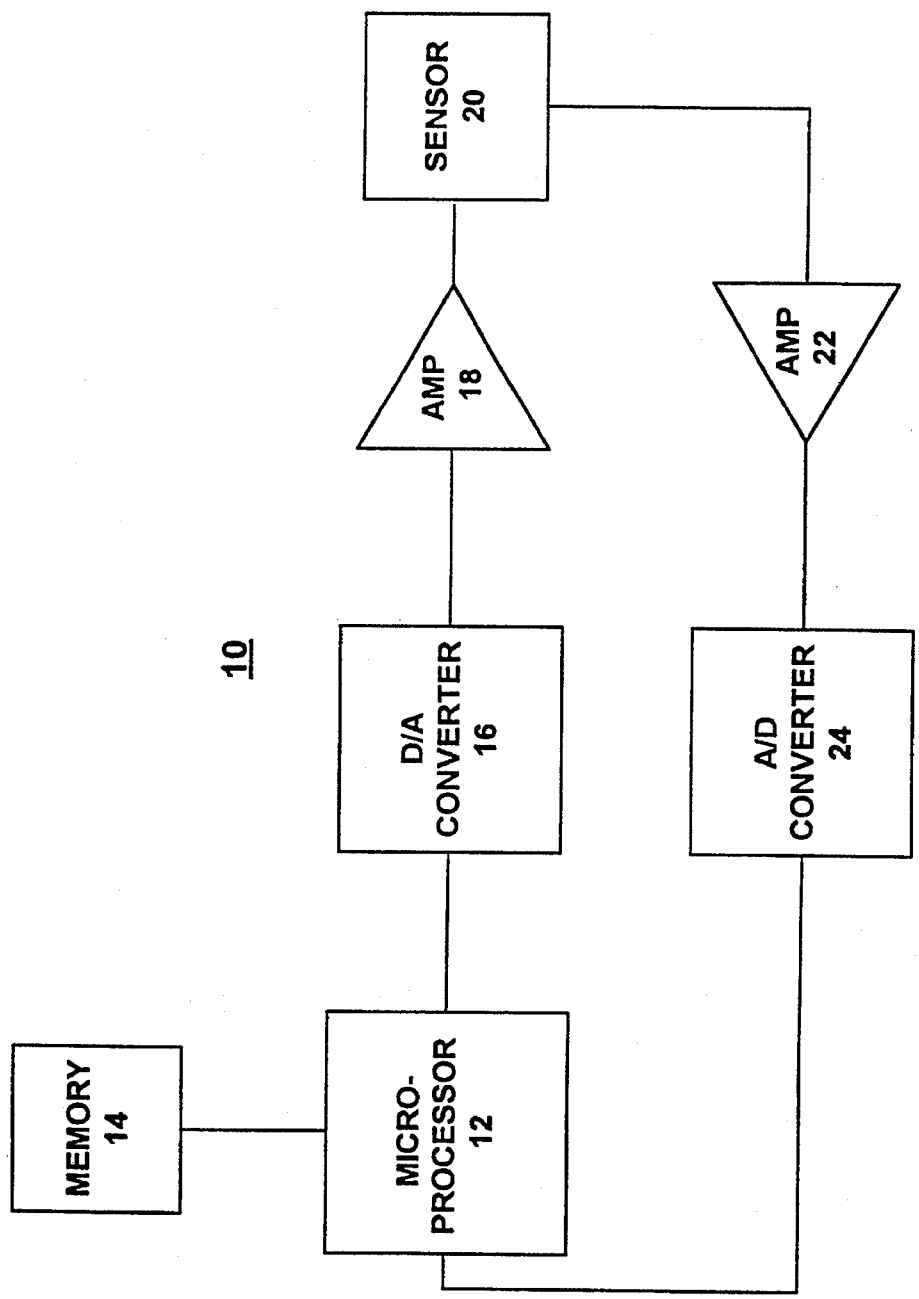
FIG. 2 is a block diagram representation of a device for determining analyte values employed to perform the method of the invention.
Figure 3:
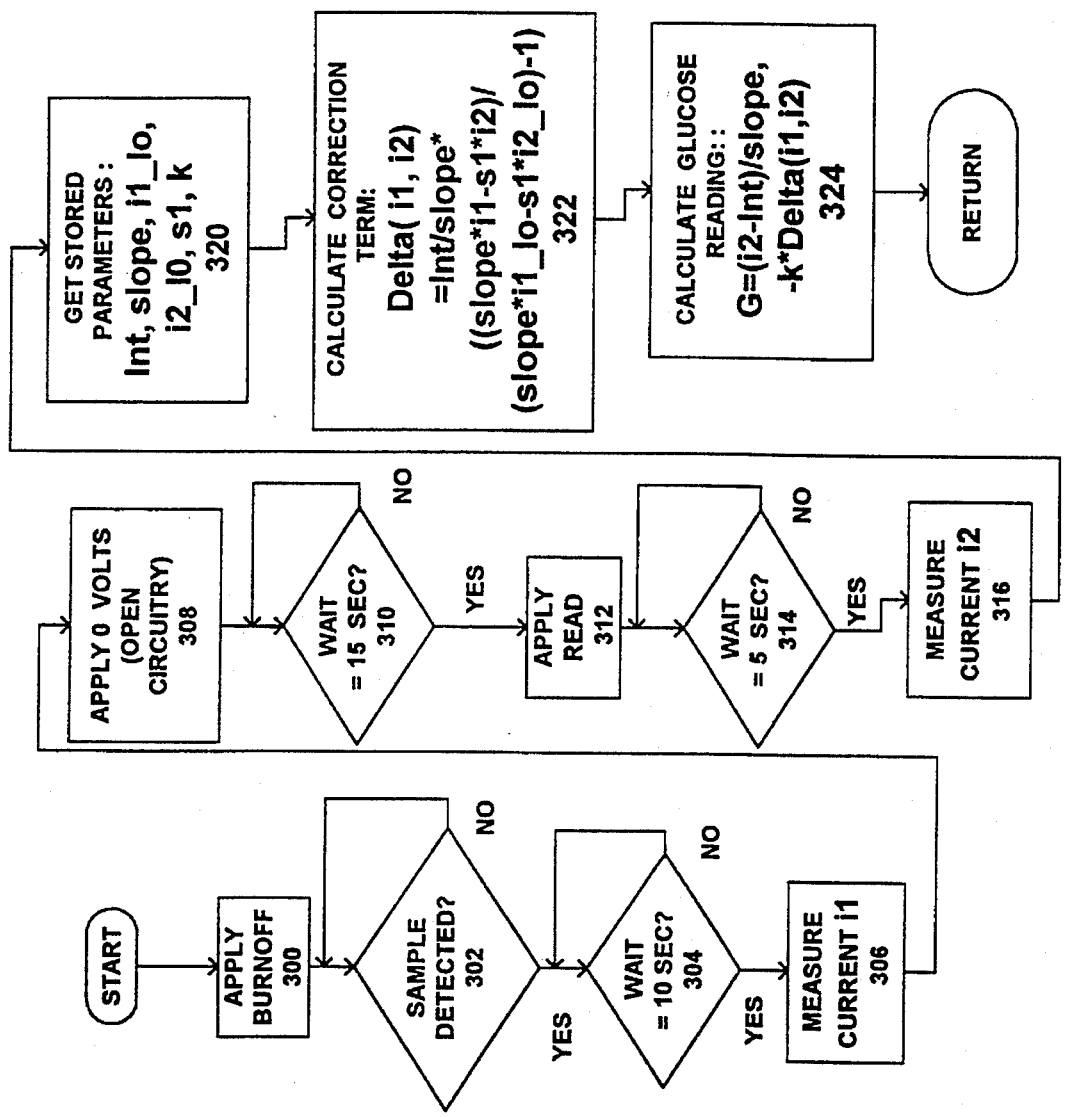
FIG. 3 is a flow chart illustrating the sequential steps performed by a processor of FIG. 2 in accordance with the method of the invention.

A device capable of carrying out the invention is represented by FIG. 2. Referring to FIG. 2, there is shown a block diagram representation of a device for accurately determining analyte values designated as a whole by the reference character 10 and arranged in accordance with principles of the present invention. Device 10 includes a microprocessor 12 together with a memory device 14. Microprocessor 12 is suitably programmed to perform the method of the invention as illustrated in FIG. 3. Various commercially available devices, such as a DS5000 microcontroller manufactured by Dallas Semiconductor, can be used for the microprocessor 12 and memory 14. Memory 14 can be included within the microprocessor 12 or separately provided as illustrated in FIG. 2.

Digital data from the microprocessor 12 is applied to a digital-to-analog (D/A) converter 16. D/A converter 16 converts the digital data to an analog signal. An amplifier 18 coupled to the D/A converter 16 amplifies the analog signal. The amplified analog signal output of amplifier 18 is applied to a sensor 20.

Sensor 20 is coupled to an amplifier 22. The amplified sensed signal is applied to an analog-to-digital (A/D) converter 24 that converts the amplified, analog sensor signal to a digital signal. The digital signal is applied to the microprocessor 12.

Various commercially available devices can be used for D/A converter 16, amplifiers 18 and 20 and A/D converter 24. For example, a device type PM-752F4FS manufactured by PMI can be used for D/A converter 16. Operational amplifier device type TL074AC manufactured and sold by Linear Technology can be used for amplifiers 18 and 22. A device type MAX 135 CWI manufactured and sold by Maxum can be used for the A/D converter 24.

Referring also to FIG. 3, there are shown the sequential steps for accurate analyte determination of the invention. Initially microprocessor 12 applies a burnoff pulse, for example a potential of 0.4 volts, to the sensor 20 as indicated at a block 300. Then the microprocessor checks to identify a sample corresponding to a detected sensor threshold current value as indicated at a decision block 302. When a sample is detected at block 302, a predetermined burnoff time interval, such as 10 seconds is identified at a decision block 304. Next the current $i_1$ is measured as indicated at a block 306 and an open circuit is applied to the sensor 20 as indicated at a block 308. Then a set delay or predetermined wait time interval, such as fifteen (15) seconds is identified at a decision block 310. After the set delay, a read pulse or potential of 0.4 volts is applied to the sensor 20 as indicated at a block 312. Then a predetermined read time interval for the read pulse, such as 5 seconds is identified at a decision block 314 and the current $i_2$ is measured as indicated at a block 316. Next microprocessor 12 gets the stored parameters for a particular sensor 20 including Int, slope, $i_{1\_lo}$, $i_{2\_lo}$, $S_1$ and k, as indicated at a block 320. The correction term Delta ($i_1$, $i_2$) is calculated utilizing the stored parameters and measured burn-off current $i_1$ and read current $i_2$ as indicated block 322. Next the analyte value, such as glucose reading G, is calculated utilizing the read current $i_2$ and the calculated correction term Delta ($i_1$, $i_2$) multiplied by the selected scaling value k, as indicated at a block 324.

What is claimed is:

1. Apparatus for analyte determination in a test sample comprising:

amperometric sensor means for receiving the test sample;

timer means for identifying a burnoff time interval, a delay time interval, and a read time interval; said read time interval following said delay time interval;

voltage potential means responsive to said timer means for applying a first voltage potential which is a burnoff voltage potential to said amperometric sensor means during said burnoff time interval and for applying a second voltage potential which is a read voltage potential to said amperometric sensor means during said read time interval; said burnoff voltage potential and said read voltage potential having a common polarity;

means responsive to said timer means and said voltage potential means for measuring a first current $i_1$ resulting from said applied burnoff voltage potential and a second current $i_2$ resulting from said applied read voltage potential; and means responsive to said current measuring means for determining an analyte value of the test sample.

2. Apparatus of claim 1 further includes means for storing predetermined characteristic parameter values relating to said amperometric sensor means and means responsive to said first current $i_1$ and second current $i_2$ measuring means for calculating a bias correction value.

3. Apparatus of claim 2 wherein said analyte value determining means is responsive to said bias correction value calculating means for determining said analyte value.

4. Apparatus of claim 3 wherein said calculated bias correction value is defined by means for calculating:

$$\Delta(i_1, i_2) = \frac{Int}{slope} \cdot \frac{slope \cdot i_1 - s_1 \cdot i_2}{slope \cdot i_{1-lo} - s_1 \cdot i_{2-lo}} - 1$$

where $i_1$ represents said first current resulting from said burnoff voltage potential, $i_2$ represents said second current resulting from said read voltage potential and Int, slope, $i_{1-lo}$, $i_{2-lo}$ and $s_1$ represent said predetermined characteristic parameter values relating to said amperometric sensor means, Int being the intercept of current $i_2$, slope being the slope of current $i_2$, $i_{1-lo}$ being the average current $i_1$ at the low analyte calibration level, $i_{2-lo}$ being the average current $i_2$ at the low analyte calibration level and $s_1$ being the slope current $i_1$.

5. Apparatus of claim 4 wherein said analyte is glucose and said determined analyte value is represented by:

$$G = \frac{i_2 - Int}{slope} - k \cdot \Delta(i_1, i_2)$$

where k represents a selected bias scaling factor having a value between 0 and 1.

* * * * *